US012735692B2

(12) United States Patent
Hioki et al.

(10) Patent No.: US 12,735,692 B2

(45) Date of Patent: Sep. 15, 2026

(54) MUTANT PROTEASE AND USE THEREOF

(71) Applicant: KAO CORPORATION, Tokyo (JP)

(72) Inventors: Takahiro Hioki, Wakayama (JP); Daichi Yamashita, Utsunomiya (JP); Akihito Kawahara, Wakayama (JP)

(73) Assignee: KAO CORPORATION, Tokyo (JP)

(*) Notice: Subject to any disclaimer, the term of this patent is extended or adjusted under 35 U.S.C. 154(b) by 603 days.

(21) Appl. No.: 18/033,837

(22) PCT Filed: Oct. 6, 2021

(86) PCT No.: PCT/JP2021/036956

§ 371 (c)(1),
(2) Date: Sep. 19, 2023

(87) PCT Pub. No.: WO2022/091723

PCT Pub. Date: May 5, 2022

(65) Prior Publication Data

US 2024/0043822 A1 Feb. 8, 2024

(30) Foreign Application Priority Data

Oct. 30, 2020 (JP) ................................ 2020-182945

(51) Int. Cl.

*C12N 9/54* (2006.01)
*C12N 9/64* (2006.01)
*C12N 15/63* (2006.01)

(52) U.S. Cl.

CPC .......... *C12N 9/6489* (2013.01); *C12N 15/63* (2013.01); *C12Y 304/24032* (2013.01)

(58) Field of Classification Search

CPC ................................................... C12N 9/6489

See application file for complete search history.

(56) References Cited

U.S. PATENT DOCUMENTS 11,371,034 B2 * 6/2022 Hioki ...................... C12N 9/52
2021/0071114 A1 3/2021 Yamashita et al.
2021/0207116 A1 7/2021 Hioki et al.

FOREIGN PATENT DOCUMENTS

EP 4053295 A1 9/2022
JP H04-108387 A 4/1992
JP 2019123803 A 7/2019
JP 2020080710 A 6/2020
JP 2021069378 A 5/2021

(Continued)

OTHER PUBLICATIONS

English Translation of WO 2019/142773. Retrieved on Sep. 25, 2025.*

(Continued)

*Primary Examiner* — Yong D Pak

(74) *Attorney, Agent, or Firm* — Element IP, PLC

(57) ABSTRACT

A polypeptide having a glycine-glycine bond-degrading activity and an improved microbicidal activity, and a method for using the same. A polypeptide having an amino acid sequence having at least 80% identity to SEQ ID NO: 2, the polypeptide having a modification involving one or more amino acid residues at positions 116, 170, 172, 173, 174, 178, and/or 179 in the amino acid sequence of SEQ ID NO: 2 or a position corresponding thereto, where the polypeptide has a glycine-glycine bond-degrading activity.

7 Claims, 2 Drawing Sheets

Specification includes a Sequence Listing.

(56) References Cited

FOREIGN PATENT DOCUMENTS

| | | | |
|---|---|---|---|
| JP | 2023033187 | A | 3/2023 |
| WO | WO-2019142773 | A1 | 7/2019 |

OTHER PUBLICATIONS

Li. Molecular cloning and nucleotide sequence of the beta-lytic protease gene from Achromobacter lyticus. J Bacteriol. Nov. 1990; 172(11):6506-11 (Year: 1990).*

Fransceus. J Ind Microbiol Biotechnol. May 2017;44(4-5):687-695 (Year: 2017).*

Sanavia. Computational and Structural Biotechnology Journal, vol. 18, 2020, pp. 1968-1979. (Year: 2020).*

Studer. Residue mutations and their impact on protein structure and function: detecting beneficial and pathogenic changes. Biochem. J. (2013) 449, 581-594 (Year: 2013).*

A0A2U9TAQ8_9GAMM. UniProtKB Database. Sep. 12, 2018. (Year: 2018).*

Rawlings. Evolutionary Families of Metalloproteases. Methods in Enzymology, vol. 248, pp. 183-228, 1995. (Year: 1995).*

Hioki. Heterologous production of active form of beta-lytic protease by Bacillus subtilis and improvement of staphylolytic activity by protein engineering. Microb Cell Fact. Dec. 28, 2021;20(1):231 (Year: 2021).*

Extended European Search Report issued Sep. 11, 2024, for European Patent Application No. 21885842.1, 8 pages.

Hioki, Takahiro, et al., "Heterologous production of active form of beta-lytic protease by Bacillus subtilis and improvement of staphylolytic activity by protein engineering", Microbial Cell Factories, vol. 20, No. 1, Dec. 1, 2021, pp. 231-231, XP93197020, ISSN: 1475-2859, DOI: 10.1186/s12934-021-01724-x.

Shaoliang, Li, et al., "Purification, Staphylolytic Activity, and Cleavage Sites of α-Lytic Protease from Achromobacter lyticus", Journal of Biochemistry, vol. 122, No. 4, Oct. 1, 1997), pp. 772-778, XP93197017, ISSN: 0021-924x.

"Beta-lytic metalloendopeptidase [Lysobacter enzymogenes]", Accession: ALN56191, NCBI [online], Nov. 12, 2015, [retrieved on Oct. 27, 2021], Internet: <https://www.ncbi.nlm.nih.gov/protein/951301954>, 1 page.

Agnieszka Bera et al, "Influence of Wall Teichoic Acid on Lysozyme Resistance in *Staphylococcus aureus*", Journal of Bacteriology, vol. 189, No. 1, 2007, pp. 280-283.

International Search Report issued Nov. 9, 2021 in PCT/JP2021/036956, 3 pages.

Kashfia Ahmed et al, "Purification, Bacteriolytic Activity, and Specificity of β-Lytic Protease from *Lysobacter* sp. IB-9374", Journal of Bioscience and Bioengineering, 95(1), 2003, pp. 27-34.

Piotr Szweda et al, "Peptidoglycan hydrolases-potential weapons against *Staphylococcus aureus*", Applied Microbiology and Biotechnology, 96(5), 2012, pp. 1157-1174.

Shaoliang Li et al, "Bacteriolytic Activity and Specificity of Achromobacter β-Lytic Protease", The Journal of Biochemistry, 124(2), 1998, pp. 332-339.

* cited by examiner

MUTANT PROTEASE AND USE THEREOF

FIELD OF THE INVENTION

The present invention relates to a mutant protease and use thereof.

BACKGROUND OF THE INVENTION

*Staphylococcus aureus* is one of the most important human and animal pathogens and causes a wide range of diseases such as skin and eye infections, food poisoning, pneumonia, meningitis, endocarditis, and osteomyelitis. In addition, the emergence of a drug-resistant bacterium such as methicillin-resistant *Staphylococcus aureus* (MRSA) and the nosocomial infection therewith have become serious issues. Because of this, an enzyme which can kill *Staphylococcus aureus* by lysis is expected to have clinical, veterinary, and food engineering applications (Non Patent Literature 1).

The most widely industrially used lytic enzyme is lysozyme. However, although lysozyme has a cell wall-degrading activity against a relatively wide range of bacteria, *Staphylococcus aureus* is known to be resistant to lysozyme because of the cell wall structure thereof (Non Patent Literature 2).

On the other hand, the M23 family of proteases is a protease family defined in the MEROPS database as a protease which can degrade a glycine-glycine bond in a peptide sequence, has the activity of degrading elastin and proteoglycan of the bacterial cell wall, and is also known as a lytic enzyme. In the family, β-lytic metalloprotease (beta-lytic metallopeptidase; BLP) belonging to the M23A subfamily has been reported to have a strong lytic activity against a gram-positive bacterium such as *Staphylococcus aureus* or *Bacillus subtilis* (Non Patent Literatures 3 and 4).

Regarding an M23A subfamily protease, processing of a proprotein to a mature protein is an obstacle, and heterologous expression is difficult, but, recently, it has been found that a mature protein can be efficiently produced from a culture by introducing an M23A family protease gene into a *Bacillus* host and culturing the same (Patent Literature 1). However, no functional improvement by mutagenesis into an M23A subfamily protease has been reported so far.

(Patent Literature 1) WO 2019/142773

Non Patent Literature (Non Patent Literature 1) Szweda, Piotr et al. Applied Microbiology and Biotechnology, 2012, 96(5):1157-1174

(Non Patent Literature 2) Bera, Agnieszka et al. Journal of Bacteriology, 2007, 189(1):280-283

(Non Patent Literature 3) Li, Shaoliang et al, The Journal of Biochemistry, 1998, 124(2):332-339

(Non Patent Literature 4) Ahmed, Kashfia et al. Journal of Bioscience and Bioengineeing, 2003, 95(1):27-34

SUMMARY OF THE INVENTION

The present invention relates to the following.

1) A polypeptide consisting of the amino acid sequence of SEQ ID NO: 2 or an amino acid sequence having at least 80% identity thereto, the polypeptide having any modification selected from the group consisting of:

a modification of an amino acid residue at position 116 in the amino acid sequence of SEQ ID NO: 2 or a position corresponding thereto;

a modification of amino acid residues at position 170 in the amino acid sequence of SEQ ID NO: 2 or a position corresponding thereto, position 172 or a position corresponding thereto, position 173 or a position corresponding thereto, position 174 or a position corresponding thereto, position 178 or a position corresponding thereto, and position 179 or a position corresponding thereto;

a modification of amino acid residues at position 170 in the amino acid sequence of SEQ ID NO: 2 or a position corresponding thereto, position 172 or a position corresponding thereto, position 173 or a position corresponding thereto, and position 174 or a position corresponding thereto; and a modification of amino acid residues at position 116 in the amino acid sequence of SEQ ID NO: 2 or a position corresponding thereto, position 170 or a position corresponding thereto, position 172 or a position corresponding thereto, position 173 or a position corresponding thereto, position 174 or a position corresponding thereto, position 178 or a position corresponding thereto, and position 179 or a position corresponding thereto, and the polypeptide having a glycine-glycine bond-degrading activity.

2) A polynucleotide encoding the polypeptide according to 1).

3) A vector or a DNA fragment comprising the polynucleotide according to 2).

4) A transformant comprising the vector or the DNA fragment according to 3).

5) An antimicrobial agent comprising the polypeptide according to 1) as an active component.

6) An antimicrobial method comprising using the polypeptide according to 1).

DETAILED DESCRIPTION OF THE INVENTION

Figure 1:
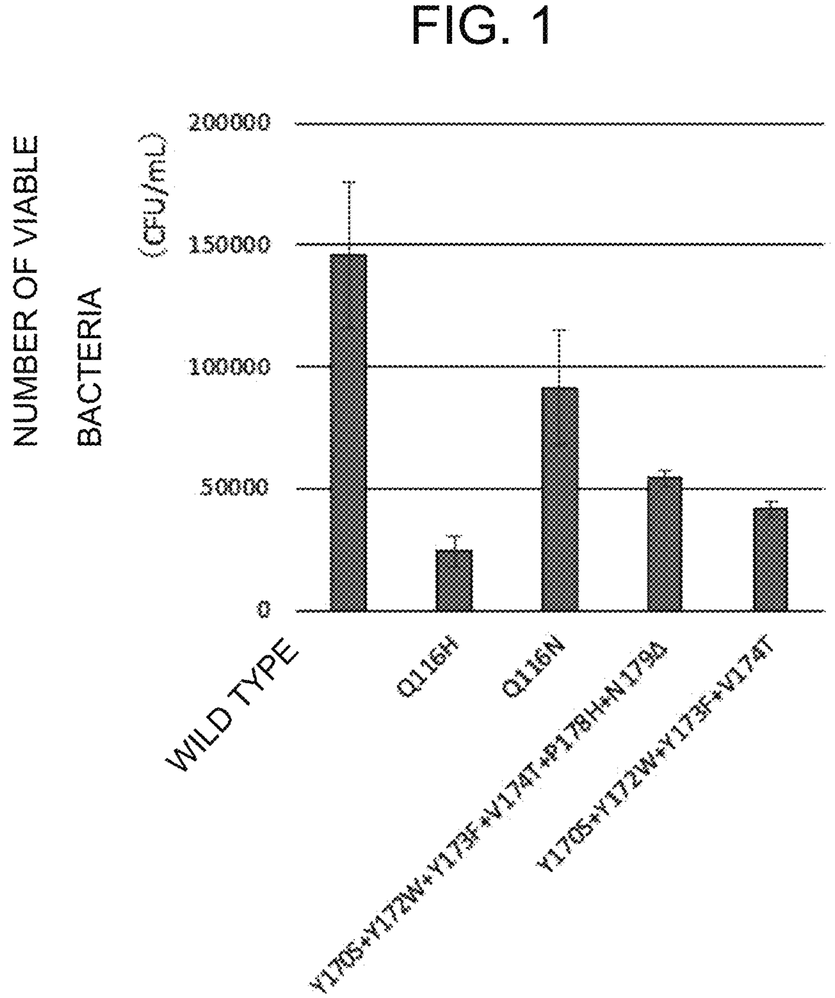
FIG. 1 shows the microbicidal activity of BLP mutants against *Staphylococcus aureus.*

All Patent Literatures, Non Patent Literatures, and other publications cited herein are incorporated herein by reference in their entirety.

As used herein, the M23A subfamily protease refers to a protease classified into the M23A subfamily, which is a subfamily of metalloproteases belonging to the M23 family, when classified in accordance with a classification method of the MEROPS database (Rawlings, Neil D., et al. "MEROPS: the database of proteolytic enzymes, their substrates and inhibitors." Nucleic acids research 42.D1 (2013): D503-D509).

As used herein, the "β-lytic metalloprotease (beta-lytic metallopeptidase; BLP)" is an enzyme also referred to as a β-lytic protease, and refers to one of the proteases belonging to the M23A subfamily. BLP has the activity of degrading a glycine-glycine bond in a peptide sequence. The activity of degrading a glycine-glycine bond can be evaluated using a method well known in the art. For example, the activity can be determined by measuring the amount of a product resulting from enzymatic degradation of a suitable substrate containing a glycine-glycine bond (for example, an oligo-glycine peptide or the FRET-GGGGG substrate described in Examples described later).

As used herein, the identity of an amino acid and a nucleotide sequence is calculated by the Lipman-Pearson method (Science, 1985, 227:1435-1441). Specifically, the identity is calculated by performing analysis using a homology analysis (Search homology) program of the genetic information processing software Genetyx-Win (Ver. Software Development Co., Ltd.) with Unit size to compare (ktup) set to 2.

As used herein, "at least 80% identity" for an amino acid sequence and a nucleotide sequence means an identity of 80% or more, preferably 85% or more, more preferably 90% or more, further more preferably 92% or more, further more preferably 94% or more, further more preferably 95% or more, further more preferably 96% or more, further more preferably 98% or more, further more preferably 99% or more, and further more preferably 99.5% or more.

As used herein, unless otherwise defined, "one or several" used for deletion, substitution, addition, or insertion of an amino acid in an amino acid sequence can mean from 1 to 40, preferably from 1 to 30, more preferably from 1 to 20, further more preferably from 1 to 10, further more preferably from 1 to 5, and further more preferably from 1 to 3. In addition, as used herein, unless otherwise defined, "one or several" used for deletion, substitution, addition, or insertion of a nucleotide in a nucleotide sequence can mean from 1 to 120, preferably from 1 to 90, more preferably from 1 to 60, further more preferably from 1 to 30, further more preferably from 1 to 15, and further more preferably from 1 to 9. As used herein, the "addition" of an amino acid or a nucleotide includes the addition of one or several amino acids or nucleotides to one end or both ends of a sequence.

As used herein, the "position corresponding" on an amino acid sequence or a nucleotide sequence can be determined by aligning (alignment of) a target sequence and a reference sequence (for example, the amino acid sequence of SEQ ID NO: 2) in such a way as to give the maximum homology. Alignment of amino acid sequences or nucleotide sequences can be carried out using a known algorithm, and a procedure therefor is known to those skilled in the art. For example, alignment can be carried out by using the Clustal W multiple alignment program (Thompson, J. D. et al, 1994, Nucleic Acids Res. 22: 4673-4680) with the default settings. Alternatively, Clustal W2 or Clustal omega, which is a revised version of Clustal W, can also be used. Clustal W, Clustal W2, and Clustal omega can be used, for example, on the website of the European Bioinformatics Institute (EBI [www.ebi.ac.uk/index.html]) or the DNA Data Bank of Japan (DDBJ [www.dbbj.nig.ac.jp/searches-j.html]) operated by the National Institute of Genetics. The position of the target sequence aligned to an arbitrary position in the reference sequence by the above alignment is regarded as a "position corresponding" to this arbitrary position.

Those skilled in the art can further fine-tune the alignment of the amino acid sequences obtained above in such a way as to optimize the same. Such optimal alignment is preferably determined in consideration of the identity or similarity of amino acid sequences, the frequency of an inserted gap, or the like. Here, the identity or similarity of amino acid sequences refers to, when two amino acid sequences are aligned, the proportion (%) of the number of positions at which identical or similar amino acid residues are present in both sequences to the number of full-length amino acid residues.

Similar amino acid residues mean amino acid residues which have a property similar to each other in terms of polarity or electric charge and can provide so-called conservative substitution, among the 20 amino acids constituting a protein. A group consisting of such similar amino acid residues is well known to those skilled in the art, and examples thereof include, but are not limited to, arginine and lysine; glutamic acid and aspartic acid; serine and threonine; glutamine and asparagine; and leucine and isoleucine.

As used herein, the "amino acid residue" refers to any of the 20 amino acid residues constituting a protein: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V).

As used herein, an amino acid position and a mutant can be represented using the officially recognized one-letter amino acid abbreviation of IUPAC as follows.

An amino acid at a predetermined position is represented by [amino acid, position]. For example, glutamine at position 116 is represented by "Q116."

The "substitution" of an amino acid is represented by [original amino acid, position, substituted amino acid]. For example, the substitution of glutamine at position 116 with histidine is represented by "Q116H."

The "deletion" of an amino acid is represented by [original amino acid, position, Δ]. For example, the deletion of asparagine at position 179 is represented by "N179Δ."

A mutant containing a plurality of modifications is represented using an addition symbol ("+"). For example, "Q116H+N179Δ" represents the substitution of glutamine at position 116 with histidine and the deletion of asparagine at position 179, respectively.

As used herein, an "operable linkage" between a control region such as a promoter and a gene means that the gene and the control region are linked in such a way that the gene can be expressed under the control of the control region. A procedure for the "operable linkage" between a gene and a control region is well known to those skilled in the art.

As used herein, "upstream" and "downstream" for a gene mean upstream and downstream, respectively, in the transcription direction of the gene. For example, a "gene located downstream of a promoter" means that the gene is present on the 3' side of the promoter in a DNA sense strand, and upstream of the gene means a region on the 5' side of the gene in a DNA sense strand.

As used herein, the term "original" used for a function, a property, or a trait of a cell is used to indicate that the function, property, or trait is originally present in the cell. In contrast, the term "foreign" is used to describe a function, a property, or a trait which is not inherent in the cell but is introduced externally. For example, a "foreign" gene or polynucleotide is a gene or a polynucleotide introduced externally into a cell. The foreign gene or polynucleotide may be derived from an organism of the same species as a cell into which the foreign gene or polynucleotide has been introduced or derived from an organism of a different species (that is, a heterologous gene or polynucleotide).

As used herein, a "parent" polypeptide of a given mutant polypeptide refers to a polypeptide which becomes the mutant polypeptide by making a predetermined mutation to an amino acid residue thereof. In other words, a "parent" polypeptide is a polypeptide before the mutation is added to become the mutant polypeptide. Similarly, a "parent" polynucleotide of a mutant polynucleotide means a polynucleotide which becomes the mutant polynucleotide by making a predetermined mutation to a nucleotide thereof. In other words, a "parent" polynucleotide is a polynucleotide before the mutation is added to become the mutant polynucleotide.

The present invention relates to a provision of a polypeptide having a glycine-glycine bond-degrading activity and an improved microbicidal activity and a method for using the same.

The present inventors found that modification of a specific amino acid residue on the amino acid sequence of BLP, which belongs to the M23A subfamily proteases and has a glycine-glycine bond-degrading activity, improves the microbicidal activity of the BLP, and completed the present invention.

The polypeptide having a glycine-glycine bond-degrading activity according to the present invention has an excellent microbicidal activity. Such a polypeptide can be used as an active component of an antimicrobial agent.

<Polypeptide Having Glycine-Glycine Bond-Degrading Activity>

The polypeptide having a glycine-glycine bond-degrading activity according to the present invention (referred to as the "polypeptide of the present invention") is a polypeptide consisting of the amino acid sequence of SEQ ID NO: 2 or an amino acid sequence having at least 80% identity thereto, having any modification selected from the group consisting of:

- a modification of an amino acid residue at position 116 in the amino acid sequence of SEQ ID NO: 2 or a position corresponding thereto;
- a modification of amino acid residues at position 170 in the amino acid sequence of SEQ ID NO: 2 or a position corresponding thereto, position 172 or a position corresponding thereto, position 173 or a position corresponding thereto, position 174 or a position corresponding thereto, position 178 or a position corresponding thereto, and position 179 or a position corresponding thereto;
- a modification of amino acid residues at position 170 in the amino acid sequence of SEQ ID NO: 2 or a position corresponding thereto, position 172 or a position corresponding thereto, position 173 or a position corresponding thereto, and position 174 or a position corresponding thereto; and
- a modification of amino acid residues at position 116 in the amino acid sequence of SEQ ID NO: 2 or a position corresponding thereto, position 170 or a position corresponding thereto, position 172 or a position corresponding thereto, position 173 or a position corresponding thereto, position 174 or a position corresponding thereto, position 178 or a position corresponding thereto, and position 179 or a position corresponding thereto.

Such a polypeptide is a mutant polypeptide which is obtained from a parent polypeptide serving as a reference, that is, a polypeptide consisting of the amino acid sequence of SEQ ID NO: 2 or an amino acid sequence having at least 80% identity thereto, by a modification of the amino acid residue at the above predetermined position, and which has the activity of degrading a glycine-glycine bond in a peptide sequence. Such a modification of the amino acid residue at the predetermined position is a modification for improving the microbicidal activity, and thus the polypeptide has an improved microbicidal activity as compared with the parent polypeptide.

In the polypeptide of the present invention, the modification site (mutation position) of an amino acid residue is any position selected from the group consisting of:

- position 116 in the amino acid sequence of SEQ ID NO: 2 or a position corresponding thereto;
- position 170 in the amino acid sequence of SEQ ID NO: 2 or a position corresponding thereto, position 172 or a position corresponding thereto, position 173 or a position corresponding thereto, position 174 or a position corresponding thereto, position 178 or a position corresponding thereto, and position 179 or a position corresponding thereto;
- position 170 in the amino acid sequence of SEQ ID NO: 2 or a position corresponding thereto, position 172 or a position corresponding thereto, position 173 or a position corresponding thereto, and position 174 or a position corresponding thereto; and
- position 116 in the amino acid sequence of SEQ ID NO: 2 or a position corresponding thereto, position 170 or a position corresponding thereto, position 172 or a position corresponding thereto, position 173 or a position corresponding thereto, position 174 or a position corresponding thereto, position 178 or a position corresponding thereto, and position 179 or a position corresponding thereto.

Here, the polypeptide consisting of the amino acid sequence of SEQ ID NO: 2 is BLP derived from *Achromobacter lyticus*, which is registered as MEROPS ID: M23.001 in the MEROPS database. Mutation positions in the polypeptide of the present invention are numbered based on the amino acid numbers in the above amino acid sequence.

The "parent polypeptide" means a reference polypeptide to which modification is made in order to yield the polypeptide of the present invention. The parent can be a natural (wild type) polypeptide or a mutant thereof.

Examples of the parent polypeptide include BLP consisting of the amino acid sequence of SEQ ID NO: 2 and a polypeptide consisting of an amino acid sequence having at least 80% identity to the amino acid sequence of SEQ ID NO: 2 and having a glycine-glycine bond-degrading activity.

A preferable example of the polypeptide consisting of an amino acid sequence having at least 80% identity to the amino acid sequence of SEQ ID NO: 2 and having a glycine-glycine bond-degrading activity is a polypeptide consisting of an amino acid sequence having 85% or more identity, more preferably 90% or more identity, further more preferably 92% or more identity, further more preferably 94% or more identity, further more preferably 95% or more identity, further more preferably 96% or more identity, further more preferably 98% or more identity, further more preferably 99% or more identity, and further more preferably 99.5% or more identity, to the amino acid sequence of SEQ ID NO: 2, and having a glycine-glycine bond-degrading activity. Another examples of the polypeptide consisting of an amino acid sequence having at least 80% identity to the amino acid sequence of SEQ ID NO: 2 and having a glycine-glycine bond-degrading activity include a polypeptide consisting of an amino acid sequence obtained by deletion, insertion, substitution, or addition of one or several amino acids in the amino acid sequence of SEQ ID NO: 2, and having a glycine-glycine bond-degrading activity.

Further examples of the polypeptide consisting of an amino acid sequence having at least 80% identity to the amino acid sequence of SEQ ID NO: 2 and having a glycine-glycine bond-degrading activity include a BLP homolog derived from *Lysobacter gummosus*

(WP_057941690.1), and a BLP homolog derived from *Lysobacter antibioticus* (WP_057970430.1).

Preferably, the parent polypeptide has Gln at position 116 in the amino acid sequence of SEQ ID NO: 2 or a position corresponding thereto, has Tyr at position 170 in the amino acid sequence of SEQ ID NO: 2 or a position corresponding thereto, has Tyr at position 172 in the amino acid sequence of SEQ ID NO: 2 or a position corresponding thereto, has Tyr at position 173 in the amino acid sequence of SEQ ID NO: 2 or a position corresponding thereto, has Val at position 174 in the amino acid sequence of SEQ ID NO: 2 or a position corresponding thereto, has Pro at position 178 in the amino acid sequence of SEQ ID NO: 2 or a position corresponding thereto, or has Asn at position 179 in the amino acid sequence of SEQ ID NO: 2 or a position corresponding thereto. More preferably, the parent BLP has Gln, Tyr, Tyr, Tyr, Val, Pro, and Asn at position 116 in the amino acid sequence of SEQ ID NO: 2 or a position corresponding thereto, position 170 or a position corresponding thereto, position 172 or a position corresponding thereto, position 173 or a position corresponding thereto, position 174 or a position corresponding thereto, position 178 or a position corresponding thereto, and position 179 or a position corresponding thereto, respectively.

The polypeptide of the present invention can be produced by modifying the amino acid residue at the above predetermined position in the amino acid sequence of the parent polypeptide. The modification of an amino acid residue carried out at the above predetermined position includes substitution, insertion, and/or deletion of an amino acid residue. Here, "substitution" means replacing an amino acid at a position with a different amino acid, "deletion" means removing an amino acid at a position, and "insertion" means adding an amino acid in such a way as to be contiguous and directly consecutive to an amino acid at a position.

The polypeptide of the present invention is preferably a polypeptide having at least 80% identity to the amino acid sequence of SEQ ID NO: 2 and having a glycine-glycine bond-degrading activity from the viewpoint of improving the microbicidal activity. In addition, the polypeptide can include any number of conservative amino acid substitutions as long as the above properties of the polypeptide are retained.

In the present invention, the modification of an amino acid residue at position 116 in the amino acid sequence of SEQ ID NO: 2 or a position corresponding thereto is preferably substitution thereof with His or Asn; the modification of an amino acid residue at position 170 or a position corresponding thereto is preferably substitution thereof with Ser; the modification of an amino acid residue at position 172 or a position corresponding thereto is preferably substitution with Trp; the modification of an amino acid residue at position 173 or a position corresponding thereto is preferably substitution thereof with Phe; the modification of an amino acid residue at position 174 or a position corresponding thereto is preferably substitution thereof with Thr; the modification of an amino acid residue at position 178 or a position corresponding thereto is preferably substitution thereof with His; and the modification of an amino acid residue at position 179 or a position corresponding thereto is preferably deletion of the amino acid residue.

Therefore, the polypeptide of the present invention is preferably a polypeptide consisting of the amino acid sequence of SEQ ID NO: 2 or an amino acid sequence having at least 80% identity thereto, the polypeptide having any modification selected from the group consisting of:

substitution of an amino acid residue at position 116 in the amino acid sequence of SEQ ID NO: 2 or a position corresponding thereto with His;

substitution of an amino acid residue at position 116 in the amino acid sequence of SEQ ID NO: 2 or a position corresponding thereto with Asn;

substitution of an amino acid residue at position 170 in the amino acid sequence of SEQ ID NO: 2 or a position corresponding thereto with Ser, substitution of an amino acid residue at position 172 or a position corresponding thereto with Trp, substitution of an amino acid residue at position 173 or a position corresponding thereto with Phe, substitution of an amino acid residue at position 174 or a position corresponding thereto with Thr, substitution of an amino acid residue at position 178 or a position corresponding thereto with His, and deletion of an amino acid residue at position 179 or a position corresponding thereto;

substitution of an amino acid residue at position 170 in the amino acid sequence of SEQ ID NO: 2 or a position corresponding thereto with Ser, substitution of an amino acid residue at position 172 or a position corresponding thereto with Trp, substitution of an amino acid residue at position 173 or a position corresponding thereto with Phe, and substitution of an amino acid residue at position 174 or a position corresponding thereto with Thr; and substitution of an amino acid residue at position 116 in the amino acid sequence of SEQ ID NO: 2 or a position corresponding thereto with His, substitution of an amino acid residue at position 170 or a position corresponding thereto with Ser, substitution of an amino acid residue at position 172 or a position corresponding thereto with Trp, substitution of an amino acid residue at position 173 or a position corresponding thereto with Phe, substitution of an amino acid residue at position 174 or a position corresponding thereto with Thr, substitution of an amino acid residue at position 178 or a position corresponding thereto with His, and deletion of an amino acid residue at position 179 or a position corresponding thereto, and the polypeptide having a glycine-glycine bond-degrading activity.

In one embodiment, the polypeptide of the present invention consists of the amino acid sequence of SEQ ID NO: 2 or an amino acid sequence having at least 80% identity thereto, has His at position 116 in the amino acid sequence of SEQ ID NO: 2 or a position corresponding thereto, and has a glycine-glycine bond-degrading activity.

In another embodiment, the polypeptide of the present invention consists of the amino acid sequence of SEQ ID NO: 2 or an amino acid sequence having at least 80% identity thereto, has Asn at position 116 in the amino acid sequence of SEQ ID NO: 2 or a position corresponding thereto, and has a glycine-glycine bond-degrading activity.

In another embodiment, the polypeptide of the present invention consists of the amino acid sequence of SEQ ID NO: 2 or an amino acid sequence having at least 80% identity thereto, has Ser at position 170 in the amino acid sequence of SEQ ID NO: 2 or a position corresponding thereto, Trp at position 172 or a position corresponding thereto, Phe at position 173 or a position corresponding thereto, Thr at position 174 or a position corresponding thereto, His at position 178 or a position corresponding thereto, and an amino acid residue at position 179 or a position corresponding thereto deleted, and has a glycine-glycine bond-degrading activity.

In another embodiment, the polypeptide of the present invention consists of the amino acid sequence of SEQ ID NO: 2 or an amino acid sequence having at least 80% identity thereto, has Ser at position 170 in the amino acid sequence of SEQ ID NO: 2 or a position corresponding thereto, Trp at position 172 or a position corresponding thereto, Phe at position 173 or a position corresponding thereto, and Thr at position 174 or a position corresponding thereto, and has a glycine-glycine bond-degrading activity.

In another embodiment, the polypeptide of the present invention consists of the amino acid sequence of SEQ ID NO: 2 or an amino acid sequence having at least 80% identity thereto, has His at position 116 in the amino acid sequence of SEQ ID NO: 2 or a position corresponding thereto, Ser at position 170 or a position corresponding thereto, Trp at position 172 or a position corresponding thereto, Phe at position 173 or a position corresponding thereto, Thr at position 174 or a position corresponding thereto, His at position 178 or a position corresponding thereto, and an amino acid residue at position 179 or a position corresponding thereto deleted, and has a glycine-glycine bond-degrading activity.

<Polynucleotide Encoding the Polypeptide of the Present Invention>

The polypeptide of the present invention can be produced by making the above modification to the parent polypeptide using various mutagenesis techniques known in the art. For example, the polypeptide of the present invention can be produced by mutating a polynucleotide encoding an amino acid residue to be modified in a polynucleotide encoding the amino acid sequence of the parent polypeptide to a polynucleotide encoding the amino acid residue after modification, and further expressing a polypeptide from the resulting mutated gene.

In the present invention, various mutagenesis techniques known in the art can be used as means for mutating an amino acid residue of the parent polypeptide. For example, a polynucleotide encoding the polypeptide of the present invention can be obtained by, in a polynucleotide encoding the amino acid sequence of the parent polypeptide (hereinafter, also referred to as the parent gene), mutating a nucleotide sequence encoding an amino acid residue to be mutated to a nucleotide sequence encoding a mutated amino acid residue.

The introduction of the target mutation into the parent gene can basically be carried out by using various site-directed mutagenesis methods well known to those skilled in the art. The site-directed mutagenesis method can be carried out by any method such as an inverse PCR method or an annealing method. A commercially available kit for site-directed mutagenesis (for example, a QuickChange II Site-Directed Mutagenesis Kit or a QuickChange Multi Site-Directed Mutagenesis Kit from Stratagene, or the like) can also be used.

The site-directed mutagenesis into the parent gene can most generally be carried out by using a mutation primer containing a nucleotide mutation to be introduced. The mutation primer may be designed to be annealed to a region including a nucleotide sequence encoding an amino acid residue to be mutated in the parent gene and to include a nucleotide sequence having a nucleotide sequence (codon) encoding a mutated amino acid residue instead of the nucleotide sequence (codon) encoding the amino acid residue to be mutated. The nucleotide sequences (codons) encoding unmutated and mutated amino acid residues can be appropriately recognized and selected by those skilled in the art based on an ordinary textbook or the like. Alternatively, for site-directed mutagenesis, a method involving linking DNA fragments, obtained by amplifying the upstream side and the downstream side of a mutation site separately using two complementary primers including a nucleotide mutation to be introduced, into one by SOE (splicing by overlap extension)-PCR (Gene, 1989, 77(1):p 61-68) can also be used.

A template DNA containing the parent gene can be prepared by extracting genomic DNA from a microorganism producing the above BLP or BLP homolog by a conventional method, or by extracting RNA and synthesizing cDNA by reverse transcription. Alternatively, a corresponding nucleotide sequence may be chemically synthesized based on the amino acid sequence of the parent polypeptide and used as the template DNA. A DNA sequence including a nucleotide sequence encoding BLP consisting of the amino acid sequence of SEQ ID NO: 2 is shown in SEQ ID NO: 1. In the nucleotide sequence of SEQ ID NO: 1, the nucleotide sequence from position 595 to position 1134 is a nucleotide sequence encoding BLP consisting of the amino acid sequence of SEQ ID NO: 2.

The primer for mutation can be prepared by a well-known oligonucleotide synthesis method such as the phosphoramidite method (Nucleic Acids Research, 1989, 17:7059-7071). Such primer synthesis can also be carried out by using, for example, a commercially available oligonucleotide synthesizer (manufactured by ABI, or the like). A polynucleotide encoding the polypeptide of the present invention having a target mutation can be obtained by using a primer set including the primer for mutation and carrying out site-directed mutagenesis as described above using the parent gene as a template DNA.

The polynucleotide encoding the polypeptide of the present invention can include a single-stranded or double-stranded DNA, cDNA, RNA, or another artificial nucleic acid. The DNA, cDNA, and RNA may be chemically synthesized. In addition, the above polynucleotide may also include a nucleotide sequence of an untranslated region (UTR) in addition to an open reading frame (ORF). In addition, the above polynucleotide may be codon-optimized in accordance with the species of a transformant for producing the polypeptide of the present invention. Information on codons used by various organisms can be obtained from the Codon Usage Database ([www.kazusa.or.jp/codon/]).

BLP is first expressed as a proprotein, and the proregion thereof is cleaved by self-processing to convert the proprotein into a mature protein. The proregion refers to a region which contributes to the formation of a conformation of a mature protein region located downstream of the proregion on the proprotein. Therefore, another example of the polynucleotide encoding the polypeptide of the present invention is a polynucleotide in which a polynucleotide encoding a polypeptide functioning as a proregion of BLP has been linked upstream of the above polynucleotide encoding the polypeptide of the present invention. Examples of the polynucleotide encoding a polypeptide functioning as a proregion of the BLP include a polynucleotide consisting of the nucleotide sequence of SEQ ID NO: 1, from position 73 to position 594, a polynucleotide consisting of a nucleotide sequence having at least 80% identity to the nucleotide sequence of SEQ ID NO: 1, from position 73 to position 594 and encoding a polypeptide functioning as a proregion of BLP, and a polynucleotide consisting of a nucleotide sequence of SEQ ID NO: 1, from position 73 to position 594 with deletion, substitution, or addition of one or several nucleotides and encoding a polypeptide functioning as a proregion of BLP.

A further example of the polynucleotide encoding the polypeptide of the present invention includes a polynucleotide in which a polynucleotide encoding a polypeptide functioning as a secretion signal and a proregion of BLP has been linked upstream of the above polynucleotide encoding the polypeptide of the present invention. Examples of the polynucleotide encoding a polypeptide functioning as a secretion signal and a proregion of the BLP include a polynucleotide consisting of the nucleotide sequence of SEQ ID NO: 1, from position 1 to position 594, a polynucleotide consisting of a nucleotide sequence having at least 80% identity to the nucleotide sequence of SEQ ID NO: 1, from position 1 to position 594 and encoding a polypeptide functioning as a secretion signal and a proregion of BLP, and a polynucleotide consisting of a nucleotide sequence of SEQ ID NO:1, from position 1 to position 594 with deletion, substitution, or addition of one or several nucleotides and encoding a polypeptide functioning as a secretion signal and a proregion of BLP.

<Vector or DNA Fragment>

The obtained polynucleotide encoding the polypeptide of the present invention can be incorporated into a vector. The vector containing the above polynucleotide is a vector which can stably retain the gene, can be replicated and maintained in a host microorganism, and can stably express the polypeptide of the present invention. Examples of such a vector include a shuttle vector such as pHA3040SP64, pHSP64R, or pASP64 (JP-B-3492935), pHY300PLK (expression vector which can transform both *Escherichia coli* and *Bacillus subtilis*; Jpn J Genet, 1985, 60:235-243), or pAC3 (Nucleic Acids Res, 1988, 16:8732); and a vector which can be used for transformation of a *Bacillus* bacterium such as pUB110 (J Bacteriol, 1978, 134:318-329) or pTA10607 (Plasmid, 1987, 18:8-15). In addition, a vector derived from *Escherichia coli* (for example, pET22b(+), pBR322, pBR325, pUC57, pUC118, pUC119, pUC18, pUC19, or pBluescript) can also be used. Among these, the vector is preferably a vector which can be used for transformation of a *Bacillus* bacterium from the viewpoint of the production efficiency of the polypeptide of the present invention.

The vector can include a DNA replication initiation region or a DNA region including an origin of replication. Alternatively, in the vector, a control sequence such as a promoter region for initiating transcription of the gene, a terminator region or a secretion signal region for secreting an expressed protein extracellularly may be operably linked upstream of the polynucleotide encoding the polypeptide of the present invention.

The type of a control sequence such as the promoter region, terminator, or secretion signal region is not particularly limited, and a usually used promoter or secretion signal sequence can be appropriately selected and used depending on the host to be introduced. For example, preferable examples of a control sequence which can be incorporated into the vector include a promoter, a secretory signal sequence, or the like of the cellulase gene of a *Bacillus* sp.KSM-S237 strain.

Alternatively, into the vector of the present invention, a marker gene for selecting a host into which the vector has been appropriately introduced (for example, a gene resistance to a drug such as ampicillin, neomycin, kanamycin, or chloramphenicol) may be further incorporated. Alternatively, when an auxotrophic strain is used as a host, a gene encoding a synthase of a required nutrient may be incorporated into the vector as a marker gene. Alternatively, when a selective medium which requires a specific metabolism for growth is used, a gene related to the metabolism may be incorporated into the vector as a marker gene. Examples of such a metabolism-related gene include an acetamidase gene for using acetamide as a nitrogen source.

The linkage of the polynucleotide encoding the polypeptide of the present invention with a control sequence and a marker gene can be carried out by a method known in the art such as an SOE (splicing by overlap extension)-PCR method (Gene, 1989, 77:61-68). A procedure for introducing a linked fragment into a vector is well known in the art.

<Transformant>

The transformant of the present invention can be obtained by introducing a vector containing a polynucleotide encoding the polypeptide of the present invention into a host, or by introducing a DNA fragment containing a polynucleotide encoding the polypeptide of the present invention into the genome of a host.

The host microorganism is not particularly limited, and examples thereof include a gram-positive bacterium such as *Bacillus* (for example, *Bacillus subtilis*), a gram-negative bacterium such as *Escherichia coli, Streptomyces*, and a fungus such as *Saccharomyces* (yeast) or *Aspergillus* (mold). The host is preferably a microorganism of the same species or the same genus as a microorganism from which the parent gene encoding the amino acid sequence of the parent polypeptide of the polypeptide of the present invention to be introduced into the host is derived, *Escherichia coli*, or a *Bacillus* bacterium, and more preferably a *Bacillus* bacterium. Further, a *Bacillus* bacterium having a low production of a protease other than the polypeptide of the present invention to be introduced is preferable. Preferable examples thereof include a *Bacillus subtilis* strain in which one or more genes selected from aprX, aprE, nprB, nprE, vpr, mpr, epr, and wprA of *Bacillus subtilis* have been deleted or inactivated.

As a method for introducing a vector into a host, a method usually used in the art such as a competent cell method, an electroporation method, a protoplast method, a particle gun method, or a PEG method can be used. By selecting a strain into which a vector has been appropriately introduced using the expression of a marker gene, auxotrophy, or the like as an indicator, the target transformant into which the vector has been introduced can be obtained.

Alternatively, a fragment in which a polynucleotide encoding the polypeptide of the present invention, a control sequence, and a marker gene have been linked can also be directly introduced into the genome of a host. For example, by the SOE-PCR method or the like, a DNA fragment in which a sequence complementary to the genome of a host has been added to both ends of the linked fragment is constructed, this is introduced into the host to cause homologous recombination between the host genome and the DNA fragment, and thereby, the polynucleotide encoding the polypeptide of the present invention is introduced into the genome of the host.

When the transformant thus obtained into which the polynucleotide encoding the polypeptide of the present invention or a vector containing the same has been introduced is cultured in an appropriate culture medium, a gene encoding the protein on the vector is expressed to produce the polypeptide of the present invention. The medium used for culturing the transformant can be appropriately selected by those skilled in the art according to the type of the microorganism of the transformant.

Alternatively, the polypeptide of the present invention may be expressed from the polynucleotide encoding the polypeptide of the present invention or a transcription product thereof by using a cell-free translation system. The "cell-free translation system" is an in vitro transcription translation system or an in vitro translation system constructed by adding a reagent such as an amino acid necessary for protein translation to a suspension obtained by mechanically destroying a cell serving as a host.

The polypeptide of the present invention produced in the culture or the cell-free translation system can be isolated or purified by using common methods used for protein purification, such as centrifugation, ammonium sulfate precipitation, gel chromatography, ion exchange chromatography, and affinity chromatography, singly or appropriately in combinations thereof. At this time, when the gene encoding the polypeptide of the present invention and the secretion signal sequence are operably linked on the vector in the transformant, the produced protein is secreted extracellularly and thus can be collected more easily from the culture. The protein collected from the culture may be further purified by known means.

<Antimicrobial Agent>

As described above, BLP is known to have a lytic activity against a gram-positive bacterium (Non Patent Literatures 3 and 4). In addition, as shown in Examples described later, the polypeptide of the present invention has an improved microbicidal activity due to lysis as compared with the parent polypeptide. Therefore, the polypeptide of the present invention is useful as an antimicrobial enzyme and can be an antimicrobial agent. In addition, the polypeptide of the present invention can be used to produce an antimicrobial agent. That is, the polypeptide of the present invention can be used for antimicrobial purpose.

In the present invention, "antimicrobial" is a term which includes any of the concepts of "lytic", "microbicidal", and "sterile," which kill a microorganism, and "microbiostatic" and "specifically microbiostatic," which suppress the development, growth, and proliferation of a microorganism. Preferable examples of the antimicrobial agent include a microbicidal agent.

The antimicrobial activity or the microbicidal activity can be evaluated by using a method well known in the art. For example, the antimicrobial activity or the microbicidal activity can be evaluated by adding a test bacterium to a test solution containing a target enzyme, treating the test solution for a predetermined time, then serially diluting the test solution, culturing the test bacterium in an appropriate solid culture medium, and measuring the number of colonies generated to determine the number of viable bacteria.

Examples of a subject of the above "use" include a human, a non-human animal, a specimen derived therefrom, and an article. Use in a human or a non-human animal may be therapeutic use or non-therapeutic use. "Non-therapeutic" is a concept which does not include medical practice, that is, a concept which does not include a method for operating, treating, or diagnosing a human, and more specifically a concept which does not include a method for operation, treatment, or diagnosis of a human carried out by a doctor or a person instructed by a doctor. In addition, examples of the article include a commodity, a medical supply, a home appliance/electric appliance, a fixture (a door, a sliding door, a doorknob, or the like), and housing equipment (a bathroom, a kitchen, a washroom, a toilet, or the like).

The bacterium against which the antimicrobial agent of the present invention exhibits an antimicrobial activity is preferably a gram-positive bacterium. The gram-positive bacterium is not particularly limited, and examples thereof include a *staphylococcus* such as *Staphylococcus aureus* or *Staphylococcus epidermidis*; a *streptococcus* such as *Streptococcus pneumoniae, Streptococcus viridans, Streptococcus pyogenes*, or *Streptococcus agalactiae*; an *Enterococcus* bacterium such as *Enterococcus faecalis*; a *Bacillus* bacterium such as *Bacillus anthracis*; a *Clostridium* bacterium such as *Clostridium tetani, Clostridium perfringens*, or *Clostridium botulinum*; a *Corynebacterium* bacterium such as *Corynebacterium diphtheriae*; and a *Listeria* bacterium such as *Listeria monocytogenes*. Among these, a *staphylococcus* is more preferable, and *Staphylococcus aureus* is further more preferable.

The antimicrobial agent of the present invention may be the polypeptide alone of the present invention, or may be an enzyme composition containing the same.

The content of the polypeptide of the present invention in the enzyme composition is not particularly limited as long as the content is an amount exhibiting an antimicrobial activity, and is preferably 0.00001% by mass or more, more preferably 0.0002% by mass or more, further more preferably 0.0005% by mass or more, further more preferably 0.001% by mass or more, further more preferably 0.005% by mass or more, and further more preferably 0.01% by mass or more, and is preferably 10% by mass or less, more preferably 1% by mass or less, and further more preferably 0.5% by mass or less, based on the total mass of the composition. In addition, the content is preferably from 0.00001 to 10% by mass, more preferably from 0.0002 to 1% by mass, further more preferably from 0.0005 to 0.5% by mass, further more preferably from 0.001 to 0.5% by mass, further more preferably 0.005 to 0.5% by mass, and further more preferably from 0.01 to 0.5% by mass.

The antimicrobial agent of the present invention can be used as an antimicrobial effective pharmaceutical, quasi-drug, cosmetic, commodity, reagent, or the like, or as a material for imparting an antimicrobial property to various products such as a pharmaceutical, a quasi-drug, a cosmetic, a commodity, a reagent, and a food. Among these, the antimicrobial agent of the present invention is preferably used as a pharmaceutical, a quasi-drug, or a cosmetic, or as a material to be blended in a pharmaceutical, a quasi-drug, or a cosmetic, and more preferably used as an agent for external use from the viewpoint of making the antimicrobial agent suitable as a pharmaceutical, a quasi-drug, or a cosmetic.

The antimicrobial agent of the present invention may be in a liquid state, a semi-solid state, or a solid state, or may be in a state in which a base material such as a sheet is impregnated therewith, and when the antimicrobial agent of the present invention is an agent for external use, examples of a specific form thereof include an ointment, a cream, an emulsion, a gel, a liquid for external use, a lotion, a spray, an aerosol for external use, a pump spray, a patch, a tape, a cataplasm, a solid for external use, a powder for external use, and a liniment. In addition, the antimicrobial agent of the present invention can also be used in a form such as a face wash, a skin lotion, a lotion, a milky lotion, a cream, a mist, a spray, a face mask, a body soap, a shampoo, a hair tonic, a cleanser, a bath salt, a soap, a toothpaste, a mouthwash, a wet tissue, a face wash sheet, or a body sheet.

Such preparations can be each obtained by a general production method directly or by mixing and dispersing the antimicrobial agent with a pharmaceutically acceptable carrier, such as various oils, a surfactant, a gelling agent, a preservative, an antioxidant, a solvent, an alcohol, water, a chelating agent, a thickener, an ultraviolet absorber, an emulsion stabilizer, a moisturizer, a pH adjuster, a dye, a fragrance, or the like, and then processing the resulting dispersion into a desired form. In addition, if necessary, an antimicrobial agent other than the polypeptide of the present invention, a plant extract, an anti-inflammatory agent, a refreshing agent, or the like can be appropriately blended in such a preparation as long as the effect of the present invention is not impaired.

The antimicrobial agent of the present invention can kill a bacterium on a subject or suppress the development, growth, and proliferation of a bacterium by contacting the subject with the antimicrobial agent. The form of contact between the antimicrobial agent and a subject is not particularly limited, and examples thereof include adding, applying, or spraying the antimicrobial agent onto the surface of the subject, immersing the subject in the antimicrobial agent, and cleaning the subject using the antimicrobial agent. Examples of the subject include the above human, non-human animal, specimen derived therefrom, or article in need of an antimicrobial property, because of the presence of a bacterium, the potential presence of a bacterium, the possibility of attachment of a bacterium, or the like.

In another aspect, the present invention provides a method for improving the antimicrobial activity of a polypeptide having a glycine-glycine bond-degrading activity. The method includes carrying out, in the amino acid sequence of SEQ ID NO: 2 or an amino acid sequence having at least 80% identity thereto, any modification selected from the group consisting of:

a modification of an amino acid residue at position 116 in the amino acid sequence of SEQ ID NO: 2 or a position corresponding thereto;

a modification of amino acid residues at position 170 in the amino acid sequence of SEQ ID NO: 2 or a position corresponding thereto, position 172 or a position corresponding thereto, position 173 or a position corresponding thereto, position 174 or a position corresponding thereto, position 178 or a position corresponding thereto, and position 179 or a position corresponding thereto;

a modification of amino acid residues at position 170 in the amino acid sequence of SEQ ID NO: 2 or a position corresponding thereto, position 172 or a position corresponding thereto, position 173 or a position corresponding thereto, and position 174 or a position corresponding thereto; and a modification of amino acid residues at position 116 in the amino acid sequence of SEQ ID NO: 2 or a position corresponding thereto, position 170 or a position corresponding thereto, position 172 or a position corresponding thereto, position 173 or a position corresponding thereto, position 174 or a position corresponding thereto, position 178 or a position corresponding thereto, and position 179 or a position corresponding thereto. The details of the modification in the method are the same as those the modification in the polypeptide of the present invention described above.

Regarding the embodiments described above, the present invention further discloses the following aspects.

<1> A polypeptide consisting of the amino acid sequence of SEQ ID NO: 2 or an amino acid sequence having at least 80% identity thereto, the polypeptide having any modification selected from the group consisting of:

a modification of an amino acid residue at position 116 in the amino acid sequence of SEQ ID NO: 2 or a position corresponding thereto;

a modification of amino acid residues at position 170 in the amino acid sequence of SEQ ID NO: 2 or a position corresponding thereto, position 172 or a position corresponding thereto, position 173 or a position corresponding thereto, position 174 or a position corresponding thereto, position 178 or a position corresponding thereto, and position 179 or a position corresponding thereto;

a modification of amino acid residues at position 170 in the amino acid sequence of SEQ ID NO: 2 or a position corresponding thereto, position 172 or a position corresponding thereto, position 173 or a position corresponding thereto, and position 174 or a position corresponding thereto; and a modification of amino acid residues at position 116 in the amino acid sequence of SEQ ID NO: 2 or a position corresponding thereto, position 170 or a position corresponding thereto, position 172 or a position corresponding thereto, position 173 or a position corresponding thereto, position 174 or a position corresponding thereto, position 178 or a position corresponding thereto, and position 179 or a position corresponding thereto, and the polypeptide having a glycine-glycine bond-degrading activity.

<2> The polypeptide according to <1>, wherein the modification is any modification selected from the group consisting of:

substitution of an amino acid residue at position 116 in the amino acid sequence of SEQ ID NO: 2 or a position corresponding thereto with His;

substitution of an amino acid residue at position 116 in the amino acid sequence of SEQ ID NO: 2 or a position corresponding thereto with Asn;

substitution of an amino acid residue at position 170 in the amino acid sequence of SEQ ID NO: 2 or a position corresponding thereto with Ser, substitution of an amino acid residue at position 172 or a position corresponding thereto with Trp, substitution of an amino acid residue at position 173 or a position corresponding thereto with Phe, substitution of an amino acid residue at position 174 or a position corresponding thereto with Thr, substitution of an amino acid residue at position 178 or a position corresponding thereto with His, and deletion of an amino acid residue at position 179 or a position corresponding thereto;

substitution of an amino acid residue at position 170 in the amino acid sequence of SEQ ID NO: 2 or a position corresponding thereto with Ser, substitution of an amino acid residue at position 172 or a position corresponding thereto with Trp, substitution of an amino acid residue at position 173 or a position corresponding thereto with Phe, and substitution of an amino acid residue at position 174 or a position corresponding thereto with Thr; and substitution of an amino acid residue at position 116 in the amino acid sequence of SEQ ID NO: 2 or a position corresponding thereto with His, substitution of an amino acid residue at position 170 or a position corresponding thereto with Ser, substitution of an amino acid residue at position 172 or a position corresponding thereto with Trp, substitution of an amino acid residue at position 173 or a position corresponding thereto with Phe, substitution of an amino acid residue at position 174 or a position corresponding thereto with Thr, substitution of an amino acid residue at position 178 or a position corresponding thereto with His, and deletion of an amino acid residue at position 179 or a position corresponding thereto.

<3> The polypeptide according to <1> or <2>, wherein the polypeptide consists of the amino acid sequence of SEQ ID NO: 2 or an amino acid sequence having at least 80% identity thereto, has His at position 116 in the amino acid sequence of SEQ ID NO: 2 or a position corresponding thereto, and has a glycine-glycine bond-degrading activity.

<4> The polypeptide according to <1> or <2>, wherein the polypeptide consists of the amino acid sequence of SEQ ID NO: 2 or an amino acid sequence having at least 80% identity thereto, has Asn at position 116 in the amino acid sequence of SEQ ID NO: 2 or a position corresponding thereto, and has a glycine-glycine bond-degrading activity.

<5> The polypeptide according to <1> or <2>, wherein the polypeptide consists of the amino acid sequence of SEQ ID NO: 2 or an amino acid sequence having at least 80% identity thereto, has Ser at position 170 in the amino acid sequence of SEQ ID NO: 2 or a position corresponding thereto, has Trp at position 172 or a position corresponding thereto, has Phe at position 173 or a position corresponding thereto, has Thr at position 174 or a position corresponding thereto, has His at position 178 or a position corresponding thereto, and has an amino acid residue at position 179 or a position corresponding thereto deleted, and has a glycine-glycine bond-degrading activity.

<6> The polypeptide according to <1> or <2>, wherein the polypeptide consists of the amino acid sequence of SEQ ID NO: 2 or an amino acid sequence having at least 80% identity thereto, has Ser at position 170 in the amino acid sequence of SEQ ID NO: 2 or a position corresponding thereto, has Trp at position 172 or a position corresponding thereto, has Phe at position 173 or a position corresponding thereto, and has Thr at position 174 or a position corresponding thereto, and has a glycine-glycine bond-degrading activity.

<7> The polypeptide according to <1> or <2>, wherein the polypeptide consists of the amino acid sequence of SEQ ID NO: 2 or an amino acid sequence having at least 80% identity thereto, has His at position 116 in the amino acid sequence of SEQ ID NO: 2 or a position corresponding thereto, has Ser at position 170 or a position corresponding thereto, has Trp at position 172 or a position corresponding thereto, has Phe at position 173 or a position corresponding thereto, has Thr at position 174 or a position corresponding thereto, has His at position 178 or a position corresponding thereto, and has an amino acid residue at position 179 or a position corresponding thereto deleted, and has a glycine-glycine bond-degrading activity.

<8> The polypeptide according to any one of <1> to <7>, wherein the sequence identity is 90% or more.

<9> The polypeptide according to any one of <1> to <8>, wherein the polypeptide has an improved antimicrobial activity as compared with a parent polypeptide.

<10> The polypeptide according to <9>, wherein the antimicrobial activity is an antimicrobial activity against a gram-positive bacterium.

<11> The polypeptide according to <9> or <10>, wherein the antimicrobial activity is an antimicrobial activity against a *staphylococcus*.

<12> The polypeptide according to any one of <9> to <11>, wherein the antimicrobial activity is an antimicrobial activity against *Staphylococcus aureus*.

<13> A method for producing a polypeptide having a glycine-glycine bond-degrading activity, the method comprising carrying out, in an amino acid sequence of SEQ ID NO: 2 or an amino acid sequence having at least 80% identity thereto, any modification selected from the group consisting of:

a modification of an amino acid residue at position 116 in the amino acid sequence of SEQ ID NO: 2 or a position corresponding thereto;

a modification of amino acid residues at position 170 in the amino acid sequence of SEQ ID NO: 2 or a position corresponding thereto, position 172 or a position corresponding thereto, position 173 or a position corresponding thereto, position 174 or a position corresponding thereto, position 178 or a position corresponding thereto, and position 179 or a position corresponding thereto;

a modification of amino acid residues at position 170 in the amino acid sequence of SEQ ID NO: 2 or a position corresponding thereto, position 172 or a position corresponding thereto, position 173 or a position corresponding thereto, and position 174 or a position corresponding thereto; and a modification of amino acid residues at position 116 in the amino acid sequence of SEQ ID NO: 2 or a position corresponding thereto, position 170 or a position corresponding thereto, position 172 or a position corresponding thereto, position 173 or a position corresponding thereto, position 174 or a position corresponding thereto, position 178 or a position corresponding thereto, and position 179 or a position corresponding thereto.

<14> The method according to <13>, wherein the modification is any modification selected from the group consisting of:

substitution of an amino acid residue at position 116 in the amino acid sequence of SEQ ID NO: 2 or a position corresponding thereto with His;

substitution of an amino acid residue at position 116 in the amino acid sequence of SEQ ID NO: 2 or a position corresponding thereto with Asn;

substitution of an amino acid residue at position 170 in the amino acid sequence of SEQ ID NO: 2 or a position corresponding thereto with Ser, substitution of an amino acid residue at position 172 or a position corresponding thereto with Trp, substitution of an amino acid residue at position 173 or a position corresponding thereto with Phe, substitution of an amino acid residue at position 174 or a position corresponding thereto with Thr, substitution of an amino acid residue at position 178 or a position corresponding thereto with His, and deletion of an amino acid residue at position 179 or a position corresponding thereto;

substitution of an amino acid residue at position 170 in the amino acid sequence of SEQ ID NO: 2 or a position corresponding thereto with Ser, substitution of an amino acid residue at position 172 or a position corresponding thereto with Trp, substitution of an amino acid residue at position 173 or a position corresponding thereto with Phe, and substitution of an amino acid residue at position 174 or a position corresponding thereto with Thr; and substitution of an amino acid residue at position 116 in the amino acid sequence of SEQ ID NO: 2 or a position corresponding thereto with His, substitution of an amino acid residue at position 170 or a position corresponding thereto with Ser, substitution of an amino acid residue at position 172 or a position corresponding thereto with Trp, substitution of an amino acid residue at position 173 or a position corresponding thereto with Phe, substitution of an amino acid residue at position 174 or a position corresponding thereto with Thr, substitution of an amino acid residue at position 178 or a position corresponding thereto with His, and deletion of an amino acid residue at position 179 or a position corresponding thereto.

<15> A polynucleotide encoding the polypeptide according to any one of <1> to <12>.

<16> A vector or a DNA fragment comprising the polynucleotide according to <15>.

<17> A transformant comprising the vector or the DNA fragment according to <16>.

<18> The transformant according to <17>, wherein the transformant is a microorganism.

<19> The transformant according to <17> or <18>, wherein the transformant is a *Bacillus* bacterium.

<20> An antimicrobial agent comprising the polypeptide according to any one of <1> to <12> as an active component.

<21> The antimicrobial agent according to <20>, wherein the antimicrobial agent is an antimicrobial agent against a gram-positive bacterium.

<22> The antimicrobial agent according to <20> or <21>, wherein the antimicrobial agent is an antimicrobial agent against a *staphylococcus*.

<23> The antimicrobial agent according to any one of <20> to <22>, wherein the antimicrobial agent is an antimicrobial agent against *Staphylococcus aureus*.

<24> The antimicrobial agent according to any one of <20> to <23>, wherein the antimicrobial agent is a microbicidal agent.

<25> The antimicrobial agent according to any one of <20> to <24>, herein the antimicrobial agent is an agent for external use.

<26> Use of the polypeptide according to any one of <1> to <12> for producing an antimicrobial agent.

<27> The polypeptide according to any one of <1> to <12> for use for antimicrobial purpose.

<28> An antimicrobial method comprising using the polypeptide according to any one of <1> to <12>.

<29> Use of the polypeptide according to any one of <1> to <12> for antimicrobial purpose.

<30> An antimicrobial method comprising contacting a subject in need thereof with the polypeptide according to any one of <1> to <12>.

<31> An antimicrobial method comprising contacting a subject in need thereof with the antimicrobial agent according to any one of <20> to <25>.

<32> A method for improving an antimicrobial activity of a polypeptide having a glycine-glycine activity, the method comprising carrying out, in an amino acid sequence of SEQ ID NO: 2 or an amino acid sequence having at least 80% identity thereto, any modification selected from the group consisting of:

a modification of an amino acid residue at position 116 in the amino acid sequence of SEQ ID NO: 2 or a position corresponding thereto;

a modification of amino acid residues at position 170 in the amino acid sequence of SEQ ID NO: 2 or a position corresponding thereto, position 172 or a position corresponding thereto, position 173 or a position corresponding thereto, position 174 or a position corresponding thereto, position 178 or a position corresponding thereto, and position 179 or a position corresponding thereto;

a modification of amino acid residues at position 170 in the amino acid sequence of SEQ ID NO: 2 or a position corresponding thereto, position 172 or a position corresponding thereto, position 173 or a position corresponding thereto, and position 174 or a position corresponding thereto; and a modification of amino acid residues at position 116 in the amino acid sequence of SEQ ID NO: 2 or a position corresponding thereto, position 170 or a position corresponding thereto, position 172 or a position corresponding thereto, position 173 or a position corresponding thereto, position 174 or a position corresponding thereto, position 178 or a position corresponding thereto, and position 179 or a position corresponding thereto.

<33> The method according to <32>, wherein the modification is any modification selected from the group consisting of:

substitution of an amino acid residue at position 116 in the amino acid sequence of SEQ ID NO: 2 or a position corresponding thereto with His;

substitution of an amino acid residue at position 116 in the amino acid sequence of SEQ ID NO: 2 or a position corresponding thereto with Asn;

substitution of an amino acid residue at position 170 in the amino acid sequence of SEQ ID NO: 2 or a position corresponding thereto with Ser, substitution of an amino acid residue at position 172 or a position corresponding thereto with Trp, substitution of an amino acid residue at position 173 or a position corresponding thereto with Phe, substitution of an amino acid residue at position 174 or a position corresponding thereto with Thr, substitution of an amino acid residue at position 178 or a position corresponding thereto with His, and deletion of an amino acid residue at position 179 or a position corresponding thereto;

substitution of an amino acid residue at position 170 in the amino acid sequence of SEQ ID NO: 2 or a position corresponding thereto with Ser, substitution of an amino acid residue at position 172 or a position corresponding thereto with Trp, substitution of an amino acid residue at position 173 or a position corresponding thereto with Phe, and substitution of an amino acid residue at position 174 or a position corresponding thereto with Thr; and substitution of an amino acid residue at position 116 in the amino acid sequence of SEQ ID NO: 2 or a position corresponding thereto with His, substitution of an amino acid residue at position 170 or a position corresponding thereto with Ser, substitution of an amino acid residue at position 172 or a position corresponding thereto with Trp, substitution of an amino acid residue at position 173 or a position corresponding thereto with Phe, substitution of an amino acid residue at position 174 or a position corresponding thereto with Thr, substitution of an amino acid residue at position 178 or a position corresponding thereto with His, and deletion of an amino acid residue at position 179 or a position corresponding thereto.

EXAMPLES

Example 1 Preparation of BLP Mutant (1) Construction of BLP Mutant Expression Plasmid A forward primer containing a mutant sequence and having a complementary sequence of 15 bases to the reverse primer at the 5' end and a reverse primer with the base immediately before the mutant sequence at the 5' end were used as a primer pair for mutagenesis. PCR was carried out using the primer pair for mutagenesis using the plasmid pHY-BLP2 described in Example 1 of WO 2019/142773 as a template. When a plurality of fragments were linked, an In-Fusion reaction was carried out using their respective PCR products in accordance with the In-Fusion and HD Cloning kit (Clontech) protocol. *Bacillus subtilis* was transformed with the PCR products or the In-Fusion reaction solution by the protoplast method to obtain a transformant carrying the target BLP mutant expression plasmid.

(2) Enzyme Production Culture

The transformant colony obtained in (1) was inoculated into 1 mL of an LB medium supplemented with tetracycline in such a way as to have a final concentration of 15 ppm, and then cultured overnight at and 150 spm. The next day, 400 μL of the resulting culture solution was inoculated into 5 mL of a 2×L-maltose medium (2% tryptone, 1% yeast extract, 1% NaCl, 7.5% maltose, 7.5 ppm manganese sulfate pentahydrate, 21 μM $ZnSO_4$, 15 ppm tetracycline; % represented (w/v) %) and cultured at 30° C. and 150 spm for 2 days, and then the culture supernatant containing the enzyme produced from the cells was collected by centrifugation.

(3) Measurement of Enzyme Activity

A FRET substrate with pentaglycine located between the fluorescent group Nma and the quenching group Lys (Dpn) [hereinafter referred to as FRET-GGGGG] (manufactured to order by PH Japan Co., Ltd.) was used as a substrate. Here, Nma refers to 2-(N-methylamino)benzoyl (Nma). In addition, Lys (Dpn) refers to a substance having 2,4-dinitrophenyl (Dnp) in the side chain of lysine (Lys). 2 μL of an enzyme solution (appropriately diluted) and 200 μL of 20 mM Tris-HCl (pH 7.5) were added to a 96-well black plate, and further, 10 μL of a FRET-GGGGG solution (1 mM FRET-GGGGG, 100 mM Tris-HCl (pH 7.5)) was added to prepare a reaction solution. The fluorescence intensity of the reaction solution was measured over time by using an infinite M200 (TECAN) at a temperature of 30° C., an excitation wavelength of 340 nm, and a measurement wavelength of 440 nm. The fluorescence intensity of a reaction solution obtained by using 20 mM Tris-HCl (pH 7.5) instead of the enzyme solution and equimolar solutions of FRETS-25-STD1 and FRETS-25-STD2 (Peptide Institute, Inc.) instead of FRET-GGGGG was measured under the same reaction conditions to prepare a calibration curve. The activity per unit (U) was defined as the amount of the enzyme required to show a change in fluorescence intensity of X/min, wherein X was the fluorescence intensity of a solution containing 1 μmol of FRETS-25-STD1 and 1 μmol of FRETS-25-STD2. The FRET-GGGGG degrading activity (U/mL) of the enzyme solution was determined.

(4) Enzyme Purification from Culture Supernatant

BLP and mutants thereof were each purified from the culture supernatant obtained in (2). The culture supernatant was buffer-exchanged with 10 mM citric acid-Na pH 6 by using Amicon Ultra having a fractional molecular weight of 10 K (Merck Millipore). An enzyme was purified from the solution after the buffer exchange by using AKTA explorer 10S (GE Healthcare). First, the solution obtained by the buffer exchange was passed through a TOYOPEARL Gigacap CM-650M column (Tosoh Corporation), and then adsorbed components were eluted by using an elution buffer (10 mM citric acid-Na pH 6, 200 mM NaCl). Among the eluted fractions, fraction solutions in which the FRET-GGGGG degrading activity was found by the activity measurement method of (3) were collected. The collected fraction solutions were buffer-exchanged with a 20 mM Tris-HCl (pH 7.5) solution by using Amicon Ultra having a fraction molecular weight of 10 K to obtain enzyme solutions containing BLP and the mutants thereof, respectively.

(5) Measurement of Concentration of Enzyme Solution

A DC Protein Assay Kit (Bio-Rad Laboratories, Inc.) was used to measure the concentration of the enzyme solution. BSA Standard Solution (WAKO) was used as the standard solution for calculating the mass of a protein.

Example 2 Microbicidal Test Against *Staphylococcus Aureus*

*Staphylococcus aureus* ATCC6538 was used as a test bacterium. The SCD medium "Daigo" for general bacterial testing (FUJIFILM Wako Pure Chemical Corporation) was used as an SCD liquid medium, the SCD agar medium "Daigo" for general bacterial testing (FUJIFILM Wako Pure Chemical Corporation) was used as an SCD agar medium, the LP diluted solution "Daigo" (FUJIFILM Wako Pure Chemical Corporation) was used as an LP diluted solution, and 20 mM Tris-HCl (pH 7.5) was used as a buffer. Buffers containing enzymes, respectively, having a final concentration of 0.5 ppm were used as test solutions. The test bacterium was shaking-cultured in the SCD liquid medium at 37° C. overnight, then collected, washed and resuspended with a buffer, and prepared to $10^{8-9}$ CFU/mL. 5 μL of the resulting bacterial suspension was added to 500 μL of each test solution and incubated at 30° C. for 30 minutes. The resulting test solution was serially diluted with the LP diluted solution and applied to the SCD agar media each in an amount of 100 μL. After incubation at 37° C. for 24 hours, the number of viable bacteria (CFU/mL) contained in 1 mL of the test solution was calculated by counting the colonies.

Figure 2:
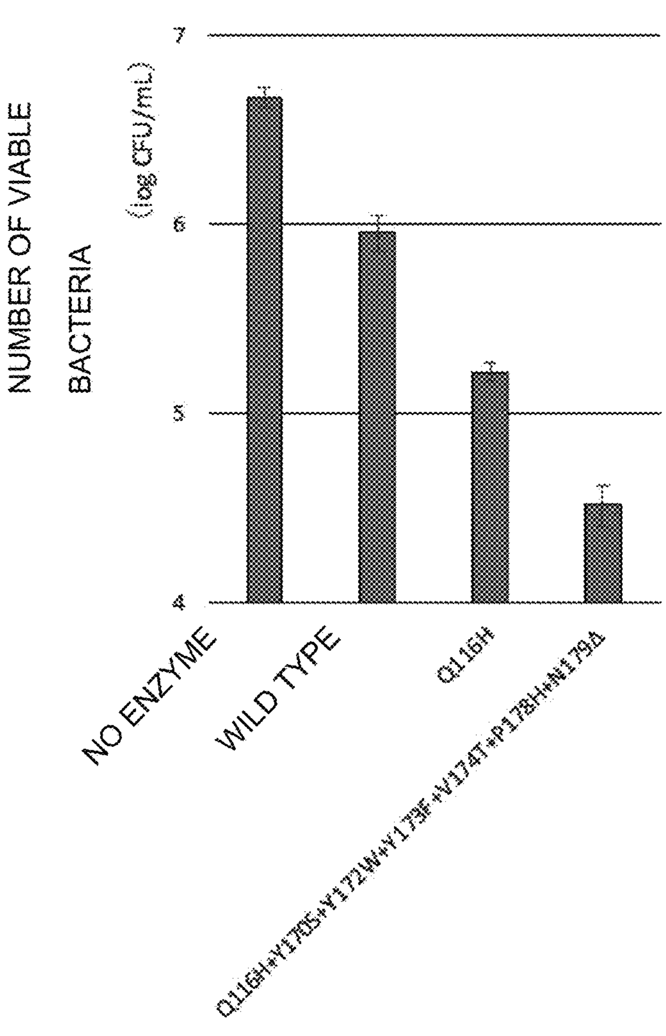
FIG. 2 shows the microbicidal activity of BLP mutants against *Staphylococcus aureus.*

The microbicidal activity against *Staphylococcus aureus* was improved for the mutants Q116H, Q116N, Y170S+Y172W+Y173F+V174T+P178H+N179Δ, and Y170S+Y172W+Y173F+V174T, as compared with wild type BLP (FIG. 1). In addition, the microbicidal activity against *Staphylococcus aureus* was further improved by combining the mutations of Q116H and Y170S+Y172W+Y173F+V174T+P178H+N1794 (FIG. 2).

Example 3 Microbicidal Test Against Methicillin-Resistant *Staphylococcus Aureus*

*Staphylococcus aureus* ATCC43300, which is methicillin-resistant *Staphylococcus aureus* (MRSA), was used as a test bacterium. The SCD medium "Daigo" for general bacterial testing (FUJIFILM Wako Pure Chemical Corporation) was used as an SCD liquid medium, the SCD agar medium "Daigo" for general bacterial testing (FUJIFILM Wako Pure Chemical Corporation) was used as an SCD agar medium, the LP diluted solution "Daigo" (FUJIFILM Wako Pure Chemical Corporation) was used as an LP diluted solution, and 20 mM Tris-HCl (pH 7.5) was used as a buffer. Buffers containing enzymes, respectively, having a final concentration of 6 ppm were used as test solutions. The test bacterium was shaking-cultured in the SCD liquid medium at 37° C. overnight, then collected, washed and resuspended with a buffer, and prepared to $10^{8-9}$ CFU/mL. 5 μL of the resulting bacterial suspension was added to 500 μL of each test solution and incubated at 30° C. for 30 minutes. The resulting test solution was serially diluted with the LP diluted solution and applied to the SCD agar media each in an amount of 100 μL. After incubation at 37° C. for 24 hours, the number of viable bacteria (CFU/mL) contained in 1 mL of the test solution was calculated by counting the colonies.

Figure 3:
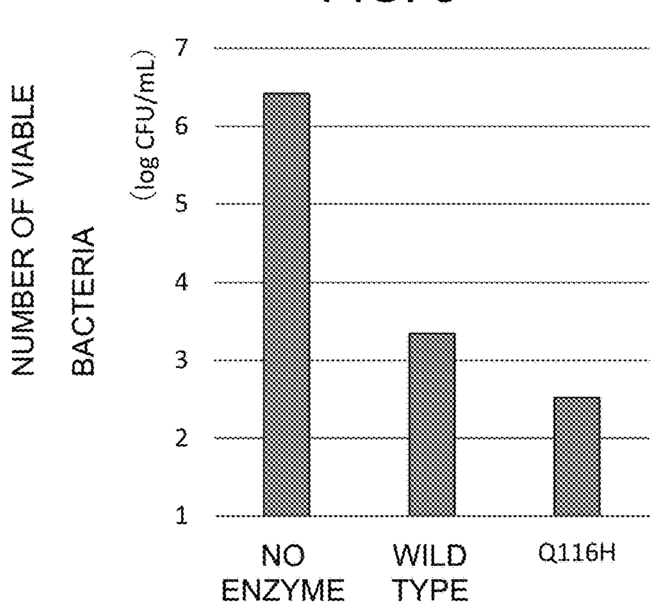
FIG. 3 shows the microbicidal activity of BLP mutants against methicillin-resistant *Staphylococcus aureus.*

The microbicidal activity against MRSA was improved for the mutant Q116H as compared with wild type BLP (FIG. 3).

The invention claimed is:

1. A polypeptide consisting of an amino acid sequence having at least 80% identity to SEQ ID NO: 2, wherein the polypeptide has a modification, relative to SEQ ID NO: 2, selected from the group consisting of (i), (ii) and (iii):

(i) substitution of an amino acid residue at position 116 in the amino acid sequence of SEQ ID NO: 2 or a position corresponding thereto with His;

(ii) substitution of an amino acid residue at position 116 in the amino acid sequence of SEQ ID NO: 2 or a position corresponding thereto with Asn; and (iii) substitution of an amino acid residue at position 116 in the amino acid sequence of SEQ ID NO: 2 or a position corresponding thereto with His, substitution of an amino acid residue at position 170 in the amino acid sequence of SEQ ID NO: 2 or a position corresponding thereto with Ser, substitution of an amino acid residue at position 172 or a position corresponding thereto with Trp, substitution of an amino acid residue at position 173 or a position corresponding thereto with Phe, substitution of an amino acid residue at position 174 or a position corresponding thereto with Thr, substitution of an amino acid residue at position 178 or a position corresponding thereto with His, and deletion of an amino acid residue at position 179 or a position corresponding thereto;

the polypeptide having a glycine-glycine bond-degrading activity.

2. A polypeptide consisting of an amino acid sequence having at least 90% identity to SEQ ID NO: 2, wherein the polypeptide has a modification, relative to SEQ ID NO: 2, selected from the group consisting of (i) and (ii):

(i) substitution of an amino acid residue at position 170 in the amino acid sequence of SEQ ID NO: 2 or a position corresponding thereto with Ser, substitution of an amino acid residue at position 172 or a position corresponding thereto with Trp, substitution of an amino acid residue at position 173 or a position corresponding thereto with Phe, substitution of an amino acid residue at position 174 or a position corresponding thereto with Thr, substitution of an amino acid residue at position 178 or a position corresponding thereto with His, and deletion of an amino acid residue at position 179 or a position corresponding thereto; and (ii) substitution of an amino acid residue at position 170 in the amino acid sequence of SEQ ID NO: 2 or a position corresponding thereto with Ser, substitution of an amino acid residue at position 172 or a position corresponding thereto with Trp, substitution of an amino acid residue at position 173 or a position corresponding thereto with Phe, and substitution of an amino acid residue at position 174 or a position corresponding thereto with Thr;

the polypeptide having a glycine-glycine bond-degrading activity, and wherein the polypeptide has an improved antimicrobial activity as compared with the corresponding polypeptide without the respective substitution.

3. An antimicrobial agent comprising the polypeptide according to claim 1 as an active component.

4. The antimicrobial agent according to claim 3, wherein the antimicrobial agent is an antimicrobial agent against a gram-positive bacterium.

5. An antimicrobial method comprising using the polypeptide according to claim 1.

6. The polypeptide according to claim 1, wherein the amino acid sequence has at least 90% identity to SEQ ID NO: 2.

7. The polypeptide according to claim 1, wherein the amino acid sequence has at least 95% identity to SEQ ID NO: 2.

* * * * *

SEQUENCE LISTING

<160> NUMBER OF SEQ ID NOS: 2

<210> SEQ ID NO 1
<211> LENGTH: 1134
<212> TYPE: DNA
<213> ORGANISM: Achromobacter lyticus

<400> SEQUENCE: 1

```
atgaaaaaaa tctcaaaagc tggtctggga ctggctctgg tctgtgctct ggcgacgatt     60

ggaggcaacg catctgctca gggacatgga ttaagcggcg aagatctggt ttactcttac    120

gatgaaatgt ttgattttga tatcgatgcc tacctggcaa aacatgcgcc gcatctgcat    180

aaacatagcg aagaaatctc tcattgggcc ggatattctg gcatttcacc gaaagttctt    240

atcgcattaa tggaacaaca gtcaggagct gtgagcgcca aaagagcaac aaatcgcccg    300

tttggcaaac ttgccagagc agatggattt ggcgcccaaa cacgcgaagt ggcgttagct    360

ctgagagaat ctctttatga acgcgatccg gatggagcca aaggcccggt cacattagcc    420

agagcaaacc cgctgcaggc actttttgaa cgctcaggag ataatgaacc ggcagcggct    480

ttaagaggag atggcgaatt tcaacttgtc tacggcagat tatttaacga accgcgccag    540

gcaaaagccg caagcgatag atttgcgaaa gctggaccgg atgttcaacc gttatctccg    600

aatggactgc ttcagtttcc gtttccgaga ggcgcatctt ggcatgtggg cggagctcat    660

acaaacacag gatcaggcaa ttatccgatg tcaagcctgg atatgtcaag aggcggaggc    720

tggggaagca atcaaaacgg caattgggtt tcagcgagcg cggctggatc ttttaaacgc    780

cattcttcat gctttgctga aattgttcat acaggcggct ggtcaacaac atactaccat    840

ctgatgaaca tccagtacaa tacaggcgcg aacgttagca tgaatacagc catcgcaaac    900

ccggctaata cacaagcgca ggctctgtgc aacggaggcc aaagcacagg accgcatgaa    960

cattggtcac tgaaacagaa cggctcattt taccatctga acggaacata cctttcaggc   1020

tatagaatca cagcgacagg cagctcttat gatacaaatt gtagccgctt ttatttgaca   1080

aaaaatggac agaactactg ctatggttat tatgtgaatc ctggaccgaa ctaa         1134
```

<210> SEQ ID NO 2
<211> LENGTH: 179
<212> TYPE: PRT
<213> ORGANISM: Achromobacter lyticus
<220> FEATURE:
<223> OTHER INFORMATION: beta-lytic metallopeptidase (BLP) mature protein

<400> SEQUENCE: 2

```
Ser Pro Asn Gly Leu Leu Gln Phe Pro Phe Pro Arg Gly Ala Ser Trp
1               5                   10                  15

His Val Gly Gly Ala His Thr Asn Thr Gly Ser Gly Asn Tyr Pro Met
            20                  25                  30

Ser Ser Leu Asp Met Ser Arg Gly Gly Gly Trp Gly Ser Asn Gln Asn
        35                  40                  45

Gly Asn Trp Val Ser Ala Ser Ala Ala Gly Ser Phe Lys Arg His Ser
    50                  55                  60

Ser Cys Phe Ala Glu Ile Val His Thr Gly Gly Trp Ser Thr Thr Tyr
65                  70                  75                  80

Tyr His Leu Met Asn Ile Gln Tyr Asn Thr Gly Ala Asn Val Ser Met
                85                  90                  95

Asn Thr Ala Ile Ala Asn Pro Ala Asn Thr Gln Ala Gln Ala Leu Cys
            100                 105                 110
```

-continued

```
Asn Gly Gly Gln Ser Thr Gly Pro His Glu His Trp Ser Leu Lys Gln
        115                 120                 125

Asn Gly Ser Phe Tyr His Leu Asn Gly Thr Tyr Leu Ser Gly Tyr Arg
    130                 135                 140

Ile Thr Ala Thr Gly Ser Ser Tyr Asp Thr Asn Cys Ser Arg Phe Tyr
145                 150                 155                 160

Leu Thr Lys Asn Gly Gln Asn Tyr Cys Tyr Gly Tyr Tyr Val Asn Pro
                165                 170                 175

Gly Pro Asn
```